(12) United States Patent
Wilhelm et al.

(10) Patent No.: US 9,091,642 B2
(45) Date of Patent: Jul. 28, 2015

(54) MEASURING TRANSDUCER FOR DETERMINING A MEASURED VARIABLE REPRESENTING AN ACTIVITY OF A TARGET ION IN A MEASURED MEDIUM

(75) Inventors: Thomas Wilhelm, Halle (DE); Michael Hanko, Dresden (DE); Stefan Wilke, Halle (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 356 days.

(21) Appl. No.: 13/566,122

(22) Filed: Aug. 3, 2012

(65) Prior Publication Data

US 2013/0032479 A1    Feb. 7, 2013

(30) Foreign Application Priority Data

Aug. 5, 2011    (DE) .......................... 10 2011 080 517

(51) Int. Cl.
  *G01N 27/333*    (2006.01)
(52) U.S. Cl.
  CPC .................................... *G01N 27/333* (2013.01)
(58) Field of Classification Search
  CPC   G01N 27/302; G01N 27/333; G01N 27/3335
  USPC ................................................. 204/416–419
  See application file for complete search history.

(56) References Cited

U.S. PATENT DOCUMENTS

| 4,713,465 A | 12/1987 | Kramer et al. |
| 2007/0144919 A1 | 6/2007 | Cheng |

FOREIGN PATENT DOCUMENTS

| CN | 2174706 Y | 8/1994 |
| CN | 201378158 Y | 1/2010 |
| CN | 201561951 U | 8/2010 |
| DE | 10018750 C2 | 11/2001 |
| DE | 102008055084 A1 | 6/2010 |
| DE | 102008055107 A1 | 7/2010 |
| JP | 2008197968 A | 8/2008 |
| JP | 2012158483 A | 8/2012 |
| WO | 97/48981 A1 | 12/1997 |
| WO | 2005106444 A1 | 11/2005 |

OTHER PUBLICATIONS

German Search Report in corresponding German Application No. 10 2011 080 517.6, dated Jun. 19, 2012.

*Primary Examiner* — J. Christopher Ball
(74) *Attorney, Agent, or Firm* — Bacon & Thomas, PLLC

(57) ABSTRACT

A measuring transducer embodied to produce and output a measurement signal dependent on an activity of a target ion present in a measured medium, wherein the measuring transducer has, in a region provided for contact with the measured medium, at least one membrane conducting the target ion; wherein the measuring transducer has a first potential sensing element and a second potential sensing element, and wherein at least one section of the second potential sensing element is arranged in the interior of the membrane and the first potential sensing element is arranged in an inner electrolyte, which is separated from the measured medium by the membrane and is in contact with the membrane.

14 Claims, 5 Drawing Sheets

MEASURING TRANSDUCER FOR DETERMINING A MEASURED VARIABLE REPRESENTING AN ACTIVITY OF A TARGET ION IN A MEASURED MEDIUM

TECHNICAL FIELD

The invention relates to a measuring transducer for determining a measured variable representing an activity of a target ion in a measured medium.

BACKGROUND DISCUSSION

The activity or concentration of a specific target ion in a measured medium is an important measured variable in environmental analytics and in a number of chemical or biochemical methods in the laboratory or in industrial processes. To a first approximation, the activity of a target ion can be set equal to the concentration of the target ion in dilute solutions.

A special case of activity measurement or concentration measurement of ions is the measurement of the pH value or pOH value of a measured medium. The pH value corresponds to the negative base 10 logarithm of the $H^+$ ion activity in the measured medium, which can be set to equal the $H^+$ ion concentration in dilute solutions. To a first approximation, the $H^+$ ion activity can be set equal to the $H^+$ ion concentration in dilute solutions. Analogous to the pH value, the pOH value is defined as the negative base 10 logarithm of the $OH^-$ ion activity or the $OH^-$ ion concentration to a good approximation for dilute solutions. The two values are related by the constant ionic product of water:

pH+pOH=14.

Starting with the pH value or the pOH value, the associated $H^+$ ion or $OH^-$ ion activities and/or the corresponding concentrations can thus be ascertained.

A measuring transducer for determining an activity of a target ion, also called an ion selective measuring transducer or an ion selective electrode in the following, includes, as a rule, a measuring half cell with an ion selective element, for example, an ion selective, solid, or polymer, membrane. The relative change of the equilibrium Galvani voltage between a measured medium and a potential sensing electrode is basically effected predominantly by the change of the activity of a specific target ion. Based on a reference potential of a basically constant potential, reference half cell, for example, a reference electrode of the second type such as the Ag/AgCl reference electrode, the activity of the target ion in the measured medium can be determined with little effort by means of a high impedance, highly accurate, voltmeter. Serving as measurement signal of such an ion selective measuring transducer for representing the activity of the target ion is thus the potential difference between the measuring half cell and the reference half cell. Ion selective electrodes are described, for example, in "Ion-selective electrodes", J. Koryta and K. Stulik, Cambridge University Press, 1983, Pg. 61 or in "Das Arbeiten mit ionenselektiven Elektroden", ("Working with Ion Selective Electrodes") K. Cammann, H. Galster, Springer, 1996.

The best known and most frequently applied ion selective measuring transducer is the pH glass electrode. The measuring half cell of the glass electrode has, as a rule, a tubular glass housing closed on one end by a membrane comprising a pH sensitive glass. The tubular glass housing is filled with an inner electrolyte, for example, a buffer solution containing chloride, and a potential sensing element, for example, a chloridized silver wire, extends into the buffer solution. A measuring half cell potential dependent on the pH value forms at the glass membrane in contact with the measured medium. As a rule, a reference electrode of second type, for example, an Ag/AgCl electrode or a calomel electrode, serves as reference half cell, which has a liquid junction between a half cell space containing the reference electrolytes and the measured medium. The potential difference between the measuring half cell potential, which can be tapped at the potential sensing element of the measuring half cell, and the reference potential (which is ideally independent of the pH value of the measured medium) of the reference half cell forms the measurement signal of the measuring transducer and is a direct measure for the $H^+$ ion activity or the pH value of the measured medium.

Although such potentiometric measuring transducers assure very precise and reliable measurement results and are well established both in the laboratory as well as in process analytics, they have a number of disadvantages. For example, defects or degradation phenomena can occur, as a rule, in the reference electrodes of second type serving as a reference half cell, degrading the quality of the measurement. For example, the inner electrolyte of the reference half cell can leak out or dry out; the liquid junction, via which the reference half cell of second type is in contact with the measured medium, can become clogged by solids, especially difficultly soluble salts; or electrode poisons can penetrate into the reference half cell via the liquid junction. In general, the potential of such reference half cells tends in practice to drift, i.e. undergo a slow, but steady change of the reference potential. Diffusion potentials and streaming potentials can also contribute to error.

In pH selective measuring transducers, which are embodied as glass electrodes, the very thin pH sensitive glass membrane is complex to manufacture and extraordinarily sensitive to handling. Breaking of the glass membrane can lead to shards, which can get into the measured medium. If the measured medium is, for example, a product manufactured in a pharmaceutical or food technical process or an intermediate product, in the case of such a glass fracture, the measured medium must be discarded, in order to prevent an endangering of the end consumer by shards in the product.

Due to the low conductivity of the pH sensitive glass membrane, it is additionally required to measure the potential difference between the leads of the measuring transducer at a very high impedance. This situation can lead to instabilities in the measurement and measured value corruptions. Due to the instances of high resistivity of the glass forming the glass membrane, there are limits to the miniaturization of the pH glass electrode, since in decreasing the glass membrane area, the resistance of the measuring half cell always becomes greater. Therefore, there has long been the need for an alternative measuring method with more robust measuring transducers for determining the pH, or pOH, value.

SUMMARY OF THE INVENTION

In view of the above described features of the prior art, it is an object of the invention to provide a measuring transducer for determining a measured variable representing an activity of a target ion in a measured medium, which measuring transducer, compared to measuring transducers known from the prior art, is easier to miniaturize, has an improved mechanical and/or chemical stability and possesses, coupled therewith, a good selectivity for the target ion.

The object is achieved by a measuring transducer embodied to produce and output a measurement signal dependent on an activity of a target ion present in a measured medium, wherein the measuring transducer has, in a region provided for contact with the measured medium, at least one membrane conducting the target ion, for example, a polymer membrane; and wherein the measuring transducer has a first potential sensing element and a second potential sensing element, wherein at least one section of the second potential sensing element is arranged in the interior of the membrane and the first potential sensing element is arranged in an inner electrolyte, which is separated from the measured medium by the membrane and is in contact with the membrane.

A potential difference measured between the first potential sensing element and second potential sensing element can serve as a measurement signal. The measuring transducer, thus, lacks a conventional reference half cell having a liquid junction and so avoids the disadvantages described initially.

Preferably, the membrane is a polymer membrane selectively conducting a target ion. A target ion conducting membrane is understood to be a membrane, e.g. a polymer membrane, whose conductivity for the target ion is higher than its conductivity for other ions present in the measured medium by a factor of at least 10, preferably at least 100, especially preferably at least 1000.

Examples of target ions include $H^+$, $OH^-$, $Na^+$, $K^+$, $NH_4^+$, $NO_3^-$, $Cl^-$, For example, the membrane can be embodied as a proton conducting polymer membrane or as a hydroxide ion conducting polymer membrane. In this case, the polymer membrane can comprise an $H^+$ ion and/or an $OH^-$ ion conducting polymer, especially a selectively conducting polymer.

Ion selective polymer membranes for the cations $Na^+$, $K^+$, $NH_4^+$ and for the anions $NO_3^-$, $Cl^-$, as well as additional cations and anions are likewise known, for example, from the above mentioned "Ion-selective electrodes", J. Koryta und K. Stulik, Cambridge University Press, 1983, Pg. 61 or in "Das Arbeiten mit ionenselektiven Elektroden", ("Working with Ion selective Electrodes") K. Cammann, H. Galster, Springer, 1996.

Proton conducting and hydroxide ion conducting polymers have been studied, especially in conjunction with the development of fuel cells. For example, Tokuyama Corporation, Shibuya, Shibuya-ku, Tokyo, Japan, offers both selectively $H^+$ ion conductive polymer membranes as well as selectively $OH^-$ ion conductive polymer membranes for use in fuel cells, as can be seen in the brochures "DMFC Membrane and Ionomer Solution", Tokuyama Corporation, February, 2011, und "Anion Conductive Membrane and Ionomer Solution", Tokuyama Corporation, February, 2011.

A large number of publications also deal with proton conducting polymers, especially for use in fuel cells. For example, in the article, "New polymeric proton conductors for water-free and high temperature fuel cells", X.-G. Sun et al., Prepr. Pap.-Am. Chem. Soc., Div. Fuel Chem. 2004, 49(2), 596, proton conductors are described, which have a backbone, to which groups serving as a proton solvent, for example, imidazole groups, and acid groups, for example fluoroalkylsulfonylimides groups, are bound by means of flexible side chains.

DE 10 2004 023 586 A1 describes a proton conductive, cross linked heteropolysiloxane with a polysiloxane basic structure, comprising sulfonic acid groups and/or carboxyl groups, which, in each case, are bound to particular Si atoms of the polysiloxane basic structure via an organic spacer, as well as either aromatic heterocyclics containing nitrogen in the ring, which are bound, in each case, via an organic spacer comprising an amide functional group to particular Si atoms of the polysiloxane basic structure, or aromatic heterocyclics containing nitrogen in the ring, which are bound, in each case, via an organic spacer to particular Si atoms of the polysiloxane basic structure. Proton conductive membranes comprising these materials are said to be distinguished by a high proton conductivity, very good chemical resistance, low gas permeability and high temperature stability. These and other proton ion or hydroxide ion conducting polymers can serve as material for the membrane of a measuring transducer of the invention.

Polymer membranes are more mechanically stable than the $H^+$ selective glass membranes of known potentiometric pH glass electrodes. Consequently, they can be advantageously applied in a potentiometric measuring transducer for pH measurement, for example, instead of the glass membrane of a pH glass electrode, whereby the danger of mechanical damage to the measuring transducer in the measurement operation or in handling the measuring transducer is significantly reduced. Furthermore, polymer membranes often have higher ion conductivity than the established glass membranes used in pH glass electrodes. This leads to the potential output by the measuring transducer having to be measured at a not as high impedance, positively affecting the stability of the measurement signal and the sensitivity to disturbance.

In an embodiment, in which the membrane is selectively proton conductive, the membrane comprises a proton conducting polymer, which is an anhydrous polymer proton conductor, and which has a basic polymeric structure, to which groups, which comprise, for example, at least one amide functional group and/or at least one ether group, serving as a proton solvent are bound by side chains, especially flexible side chains. The groups serving as a proton solvent can comprise, for example, aromatic heterocyclics, especially imidazoles, benzimidazoles or pyrazoles. In this embodiment, acid groups can be supplementally bound to the basic polymeric structure via side chains, especially flexible side chains. The additional acid grdups provide movable protons for proton conduction; they serve, thus, as a doping of the conductive polymer. The acid groups can comprise, for example, sulfonic acid groups and/or carboxyl groups.

The measuring transducer can be embodied, for example, as a potentiometric probe, which has a housing, which surrounds an inner space containing a pH buffered and preferably halogen ion containing, inner electrolyte and which is sealed by the membrane in the region intended for immersion in the measured medium, wherein at least one section of the second potential sensing element is arranged in the interior of the proton ion or hydroxide ion conducting membrane, in order to produce and to output an electrical potential dependent on the activity and/or the concentration of the target ion, for example, $H^+$ or $OH^-$, in the measured medium; wherein a first potential sensing element, for example, a silver wire, is arranged in the pH buffered inner electrolyte in order to produce and to output an electrical potential largely constant with respect to time.

Serving as a measurement signal also in this embodiment is the potential difference measured between the first potential sensing element and second potential sensing element. The measuring transducer can also be embodied to derive a signal, for example, a digitized signal, from this potential difference, and to output this derived signal as a measurement signal.

The measuring transducer can have at least one additional measuring sensor for registering a property of the inner electrolyte and/or the membrane. For example, the additional measuring sensor can register the temperature and/or the conductivity of the inner electrolyte. An additional measuring sensor can also be provided for registering the electrical resistance of the membrane or the membrane impedance.

The measuring transducer and, in given cases, the additional measuring sensor, can be connected to an evaluation circuit. The evaluation circuit can be embodied to receive the measurement signal of the measuring transducer and, in given cases, the additional measuring sensor and to output such to a superordinated unit, for example, a measurement transmitter, a programmable logic controller, a computer, a process control system or other data processor. The evaluation circuit can especially be embodied to process the measurement signal received from the measuring transducer before output to the superordinated unit, for example, to amplify and/or to convert an analog signal to a digital signal. The evaluation circuit can be correspondingly matched to the type of charge carriers, namely cations or anions, which are transported through the membrane.

The inner electrolyte preferably contains dissolved halogen ions, for example, chloride ions, wherein the first potential sensing element comprises a difficultly soluble salt of the halogen ions dissolved in the inner electrolyte. In this way, it is assured that an electrical potential largely independent of the target ion content of the measured medium and largely constant over time can be tapped at the first potential sensing element. The inner electrolyte can contain, for example, dissolved potassium chloride in a concentration of 3 mol/l and the potential sensing element can be formed as a chloridized silver wire, i.e. as a silver wire with a coating comprising difficultly soluble, silver chloride.

The second potential sensing element can comprise a first section embedded in the membrane and a second section, which is conductively connected to the first section and electrically insulated from the membrane and the inner electrolyte. To increase the contact surface between the membrane and the first section of the second potential sensing element, the first section can, for example, be embodied as a meander, spiral, loop or lattice. The potential difference between the first potential sensing element and second potential sensing element is tapped between the second section of the second potential sensing element and the first potential sensing element.

A measuring arrangement can comprise one or more measuring transducers of the embodiments described above. The measuring arrangement can furthermore comprise a measurement circuit or can be connectable to a measurement circuit, which is embodied to receive a measurement signal issued by the at least one measuring transducer, in given cases, to process and to output such to a superordinated unit, e.g. a computer, a measurement transmitter, a programmable logic controller or a process control station, and/or to a user interface, e.g. a display. The processing of the measurement signal of the one or more measuring transducers can be, for example, amplifying, smoothing, integrating or converting an analog signal to a digital signal.

In a special embodiment, the measuring arrangement can comprise a first potentiometric measuring transducer with an $H^+$ ion conducting, first membrane arranged in a region provided for contact with the measured medium, and a second potentiometric measuring transducer with an $OH^-$ ion conducting, second membrane arranged in a region provided for contact with the measured medium. This measuring arrangement allows checking the functioning of the measuring arrangement by comparing the measuring signals delivered by the two measuring transducers with one another and the utilization of the two measuring signals for predictive maintenance of the measuring arrangement. The first membrane is preferably selectively conductive for $H^+$ ions in the above mentioned sense, while the second membrane is preferably selectively conductive for $OH^-$ ions.

For example, the first potentiometric measuring transducer can have a first potential sensing element and a second potential sensing element, wherein the second potential sensing element is arranged in the interior of the first membrane in order to produce and to output an electrical potential dependent on the activity of $H^+$ ions or $OH^-$ ions present in the measured medium, and the first potential sensing element is arranged in a pH buffered, inner electrolyte, which is separated from the measured medium by the first membrane and is in contact with the membrane, in order to produce and output an electrical potential largely constant over time, and wherein the measuring arrangement is embodied to determine a first pH value and/or a first pOH value from a potential difference measured by the first measuring transducer between the first potential sensing element and the second potential sensing element. The second potentiometric measuring transducer can have a first potential sensing element and a second potential sensing element, wherein the second potential sensing element is arranged in the interior of the second membrane in order to produce and to output an electrical potential dependent on the activity of $H^+$ ions or $OH^-$ ions present in the measured medium, and the first potential sensing element is arranged in a pH buffered inner electrolyte, which is separated from the measured medium by the second membrane and is in contact with the membrane, in order to produce and output an electrical potential largely constant over time and wherein the measuring arrangement is embodied to determine a second pH value and/or a second pOH value from a potential difference measured by the second measuring transducer between the first and the second potential sensing elements.

As described above, the pH buffered inner electrolyte preferably contains dissolved halogen ions, for example, chloride ions, wherein the first potential sensing element comprises a difficultly soluble salt of the halogen ions dissolved in the inner electrolyte. In this way, it is assured that an electrical potential, which is largely independent of the target ion content of the measured medium and largely constant over time, can be tapped at the first potential sensing element. The inner electrolytes can contain, for example, dissolved potassium chloride in a concentration of 3 mol/l and the corresponding potential sensing elements can be in the form or chloridized silver wires.

The second potential sensing element of the first measuring transducer and the second potential sensing element of the second measuring transducer can comprise a first section embedded in the membrane and a second section, which is conductively connected to the first section and electrically insulated from the membrane and from the inner electrolyte. To increase the contact surface between the membrane and the first section of the second potential sensing element, the first section can be embodied with high surface area, for example, as a meander, spiral, loop or lattice. The potential difference registered between the second section of the second potential sensing element and the first potential sensing element serves as the measurement signal of the respective measuring transducer.

In an embodiment of this measuring arrangement, the first membrane can comprise a selectively proton conductive polymer and the second membrane a selectively hydroxide conductive polymer.

An extension of the measuring range of the measuring arrangement can be achieved by providing that the inner electrolyte of the first measuring transducer has a pH value that differs from the pH value of the inner electrolyte of the second measuring transducer. To achieve this expanded measuring range, the pH value of the inner electrolyte of the first measuring transducer, which has the proton conductive membrane, is preferably greater than the pH value of the second measuring transducer, which has the hydroxide conductive membrane. For example, the inner electrolyte of the first measuring transducer can have a pH value of 10 and the inner electrolyte of the second measuring transducer a pH value of 4.

BRIEF DESCRIPTION OF THE DRAWINGS

The invention will now be described in detail in the following based on the examples of embodiments shown in the drawing, the figures of which show as follows.

DETAILED DISCUSSION IN CONJUNCTION WITH THE DRAWINGS

Figure 1:
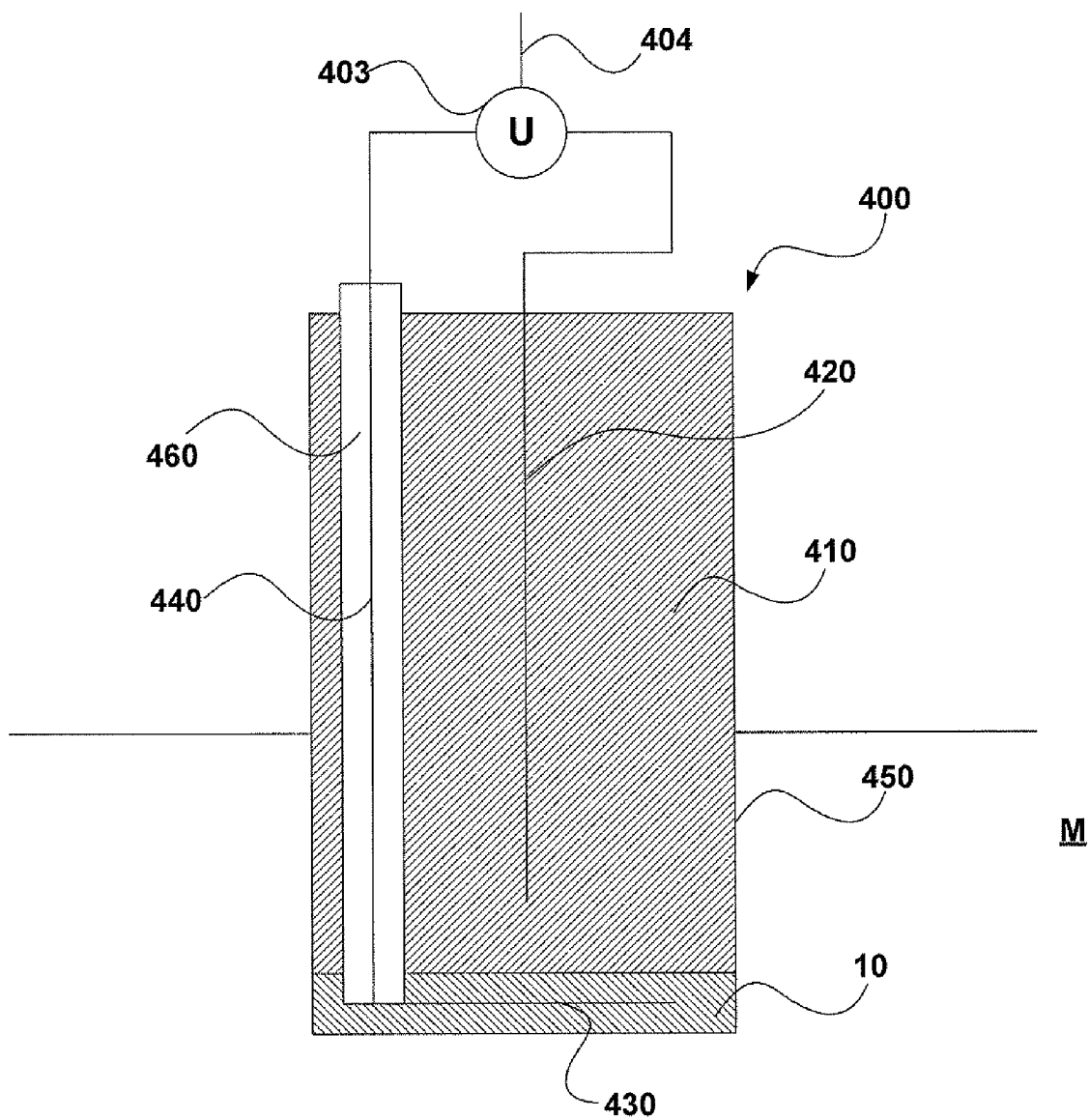
FIG. 1 a potentiometric measuring transducer for measuring a measured variable representing an activity of a target ion in a measured medium.

FIG. 1 shows a schematic representation of a measuring arrangement with a potentiometric measuring transducer 400 for measuring activity of a target ion or a measured variable representing the activity of the target ion. Examples of target ions include $H^+$, $Na^+$, $K^+$ or $NH_4^+$ or one of the anions $OH^-$, $NO_3^-$ or $Cl^-$. If the target ion is $H^+$, a measured variable representing $H^+$ activity can be, for example, the pH value. Measuring transducer 400 does not need a conventional reference half cell.

Measuring transducer 400 includes a housing 450, which contains an inner electrolyte 410. inner electrolyte 410 can be, for example, a pH buffer solution containing KCl in a concentration of 3 mol/l. The, for example, cylindrical housing 450 is sealed in a region provided for contact with the measured medium M by a target ion conducting membrane 10.

A first potential sensing element 420 extends into inner electrolyte 410. Potential sensing element 420 can comprise, for example, a chlorided silver wire, and so form an Ag/AgCl reference system with the KCl containing, inner electrolyte. A second potential sensing element 440 has a first section, which is formed by a lattice 430 of electrically conductive material, for example, platinum. Lattice 430 is embedded in membrane 10. By embedding lattice 430 in membrane 10, it is spatially isolated both from inner electrolyte 410 as well as also from the measured medium M surrounding the membrane-side, end region of measuring transducer 400, i.e. it does not directly contact either inner electrolyte 410 or measured medium M. Lattice 430 can, for example, be laminated between two membrane layers. Lattice 430 is electrically conductively connected to the measurement circuit 403 by a second section of the second potential sensing element 440, wherein the second section is formed by an electrical conductor, for example, a metal wire, e.g. a platinum wire. The electrical conductor is spatially isolated and electrically insulated from inner electrolyte 410 and membrane 10 by means of electrical insulation 460, for example, a glass tube or a jacket of synthetic material, e.g. plastic.

The membrane is selected as a function of the type of target ion. A series of polymer membranes are known for determining activity of one of the cations or anions named above. These polymer membranes selectively conduct one of these ions in the sense of the definition set forth above.

In the following, examples of embodiments will now be described, in which the membrane is proton conducting or hydroxide ion conducting. Of course, the measuring transducers described in the examples of embodiments can also be applied for measuring the activity of other cations or anions by using a membrane having a corresponding, preferably selective, conductivity for the particular target ion.

In the example described here, membrane 10 is a selectively proton conducting polymer membrane, so that the measuring transducer is suitable for measurement of $H^+$ activity in measured medium M or the pH value derived from the $H^+$ activity. In an alternative embodiment, the membrane can also comprise a selectively hydroxide conducting polymer, in order to determine a pOH value of measured medium M.

To measure the pH value of measured medium M, a membrane-side, end region of measuring transducer 400, which includes at least membrane 10, is immersed in measured medium M. Between first potential sensing element 420 and second potential sensing element 440, a potential difference forms, which is dependent on the difference of the pH values of inner electrolyte 410, on the one hand, and the measured medium M, on the other hand. The reason for this is the gradient of the $H^+$ ion concentration or activity forming from the inner side to the outer side of membrane 10, i.e. from the side of membrane 10 facing away from measured medium M to the side of membrane 10 in contact with measured medium M. The potential difference between first potential sensing element 420 and second potential sensing element 440 forms the measurement signal of the measuring transducer.

Measurement circuit 403 is conductively connected to the two potential sensing elements 420 and 440 and is embodied to output a signal U derived from the potential difference between the potential sensing elements 420 and 440 via the signal output 404.

Figure 2:
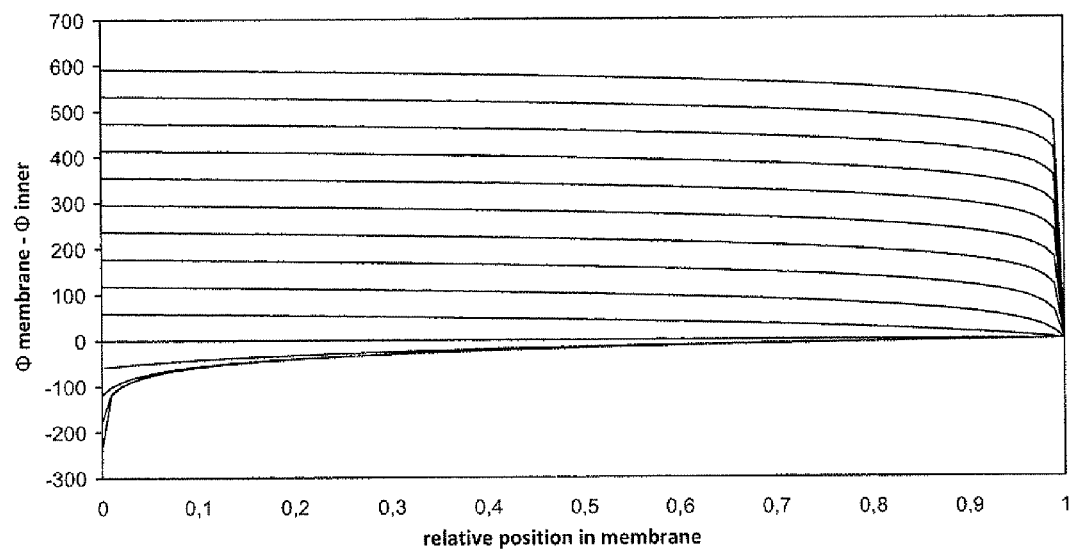
FIG. 2 a graph showing, by way of example, potential in the interior of the membrane of a measuring transducer of FIG. 1 having an $H^+$ ion conducting membrane.

FIG. 2 shows potential in the interior of the selectively proton conducting membrane 10 for different pH values of the measured medium between pH value 0 and pH value 14. The relative position within the membrane is plotted on the abscissa, wherein the relative position 0 corresponds to a point on the surface of membrane 10 in contact with measured medium M, while the relative position 1 corresponds to a point on the surface of membrane 10 facing away from measured medium M and in contact with inner electrolyte 410. The pH value of inner electrolyte 410 is pH 10 in the example described here. Potential is ascertained here via theoretical considerations based on a linear gradient of the $H^+$ concentration or activity across the membrane. In real membrane materials, the gradient does not necessarily extend linearly.

In the example shown here, lattice 430 is arranged approximately at position 0.5, i.e. in the middle of membrane 10 (see FIG. 1). From the graph illustrated in FIG. 2, it can be seen that, in the case of central relative positions in the cross section of membrane 10, the electrical potential depends strongly on the pH value of measured medium M, so long as this is less than the pH value of inner electrolyte 410.

Figure 3:
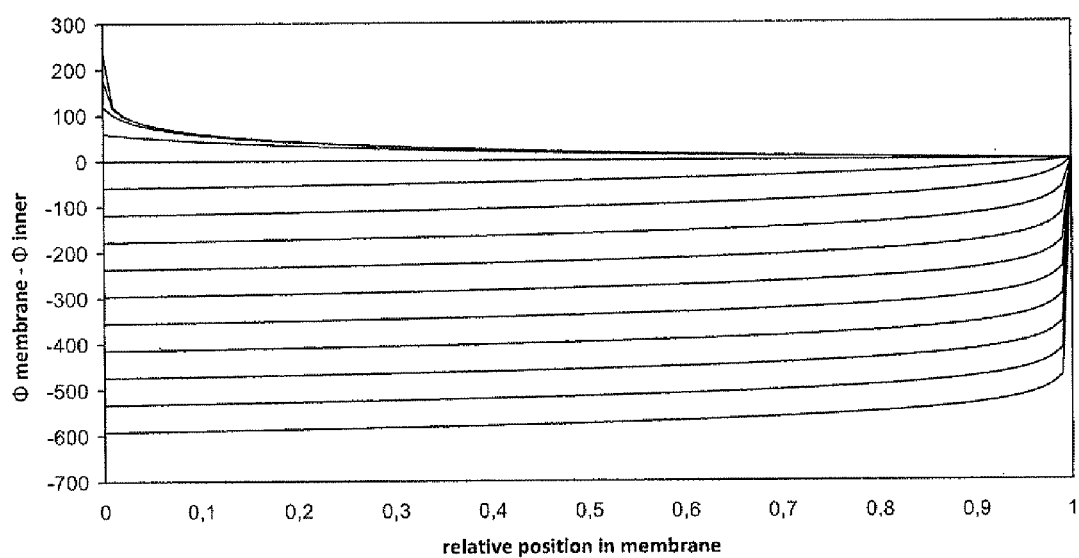
FIG. 3 a graph showing, by way of example, potential in the interior of the membrane of a measuring transducer of FIG. 1 having an $OH^-$ ion conducting membrane.

FIG. 3 shows potential in the interior of the membrane of a measuring transducer having the structure shown in FIG. 1, wherein membrane 10 is a hydroxide ion conducting membrane, instead of a proton conducting membrane, for different pH values of the measured medium. The pH values are selected to be between 0 and 14, wherein the inner electrolyte has a pH value of 4 in the example shown here. In such case, as in the graph shown in FIG. 2, a linear gradient of the $OH^-$ concentration or $OH^-$ activity across the membrane was assumed. The relative position in the membrane is plotted on the abscissa, wherein position 0 corresponds to a point on the surface of the membrane in contact with the measured medium, while position 1 corresponds to a point on the surface of the membrane facing away from measured medium M and in contact with the inner electrolyte.

As can be seen from the graph shown in FIG. 3, at a central relative position in the cross section of the membrane, the electrical potential is strongly dependent on the pH value of the measured medium, so long as this is higher than the pH value of the inner electrolyte.

In order to achieve a measuring range as large as possible for a measuring transducer having the structure illustrated in FIG. 1, it is, thus, sensible to choose a high pH value, especially equal to or greater than pH 10, for the inner electrolyte in the application of a selectively $H^+$ conducting membrane. In the application of a selectively $OH^-$ conducting membrane in a potentiometric measuring transducer of the type illustrated in FIG. 1, a low pH value, especially equal to or less than pH 4, is chosen for the inner electrolyte solution.

By means of a measuring arrangement, which has a first measuring transducer with the structure shown in FIG. 1 with a proton conducting membrane and a second measuring transducer with an identical structure, but with a hydroxide ion conducting membrane, an increased measuring range is available compared to measurement with just one of these measuring transducers, as will be described in the following.

Figure 4:
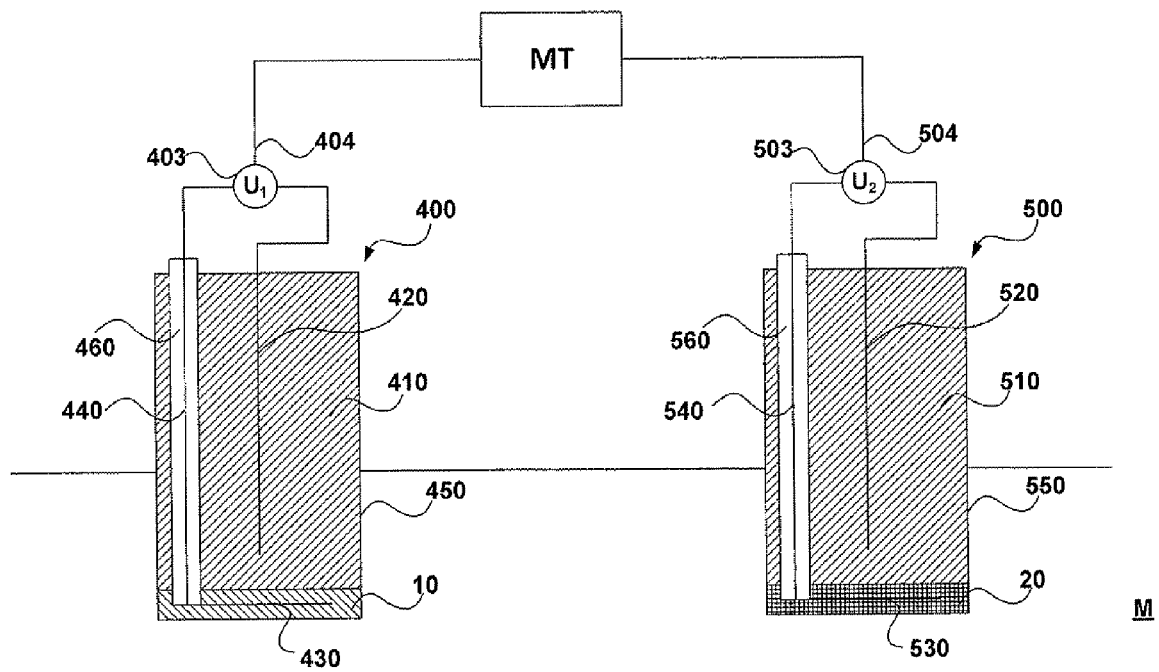
FIG. 4 a measuring arrangement having a first potentiometric measuring transducer, which has a proton conducting membrane for measuring a measured variable representing an $H^+$ activity or an $OH^-$ activity in a measured medium, and a second potentiometric measuring transducer, which has a hydroxide conducting membrane for measuring a measured variable representing an $H^+$ activity or an $OH^-$ activity in a measured medium.

FIG. 4 shows a schematic representation of a measuring arrangement having a first potentiometric measuring transducer 400 and a second potentiometric measuring transducer 500. Both measuring transducers 400, 500 are embodied for the measurement of a measured variable representing an $H^+$ content or $OH^-$ content in a measured medium, wherein first measuring transducer 400 has a proton conducting membrane 10 and second measuring transducer 500 has a hydroxide conducting membrane 20.

First measuring transducer 400 is embodied identically to the measuring transducer 400 described in FIG. 1. Measurement circuit 403 registers a first potential difference $U_1$ between the potential sensing elements 420 and 440 and sends this or a signal derived from first potential difference $U_1$ via signal output 404 of measurement circuit 403 to the superordinated unit MT. Superordinated unit MT can be a measurement transmitter.

Second measuring transducer 500 has the same structure as measuring transducer 400, i.e. it includes a housing 550, which is sealed by a membrane 20 in a region selected for immersion in measured medium M. Membrane 20 is an $OH^-$ ion conducting membrane, which can be formed, for example, by a selectively hydroxide ion conducting polymer. The housing contains an inner electrolyte 510, which can be a pH buffered aqueous solution containing a halogen salt. Inner electrolyte 510 can be, for example, a buffer solution, which contains KCl in a concentration of 3 mol/l, with the pH value 4. A potential sensing element 520, which can comprise, for example, a chlorided silver wire, extends into inner electrolyte 510, in order to form an Ag/AgCl reference system.

A second potential sensing element 540 of measuring transducer 500 has a first section, which is embodied as an electrically conductive lattice 530, comprising e.g. platinum, embedded in membrane 20. Lattice 530 is spatially isolated by the membrane both from the inner electrolyte as well as also from measured medium M surrounding the end region of the measuring transducer. Potential sensing element 540 has furthermore, electrically conductively connected to lattice 530, a second section, which can comprise, for example, a platinum wire, which is spatially isolated and electrically insulated from inner electrolyte 510 by an insulator, for example, a small glass tube or a plastic jacket. A second measurement circuit 503 produces a second measurement signal $U_2$ derived from the potential difference between the potential sensing elements 520 and 540 and forwards this signal via its signal output 504 to superordinated unit MT.

If the measuring transducers 400 and 500 with their special regions comprising membrane 10 or 20 are immersed in a measured medium, potential gradients form across membranes 10 and 20. These depend on the pH value difference between the respective inner electrolytes and the measured medium. The potential in the interior of membrane 10 of the first measuring transducer 400 is shown in FIG. 2 for different pH values of the measured medium M in the case of a pH value of inner electrolyte 410 of 10. The potential in the interior of membrane 20 of second measuring transducer 500 is presented in FIG. 3 for different pH values of measured medium M in the case of a pH value of inner electrolyte 510 of 4.

Preferably, the pH value of inner electrolyte 410 of the first measuring transducer 400 is chosen to be high, especially greater than or equal to pH 10, while the pH value of inner electrolyte 510 of the second measuring transducer is preferably chosen to be low, especially less than or equal to pH 4. Superordinated unit MT registers measuring signals $U_1$ and $U_2$ of first measuring transducer 400 and second measuring transducer 500. In this way, in the pH value range of measured medium M between pH 4 and pH 10, the opportunity arises for a dual determination of the pH value by means of the two measuring transducers. This permits a monitoring of the functionality of the measuring arrangement as well as for predictive maintenance.

Figure 5:
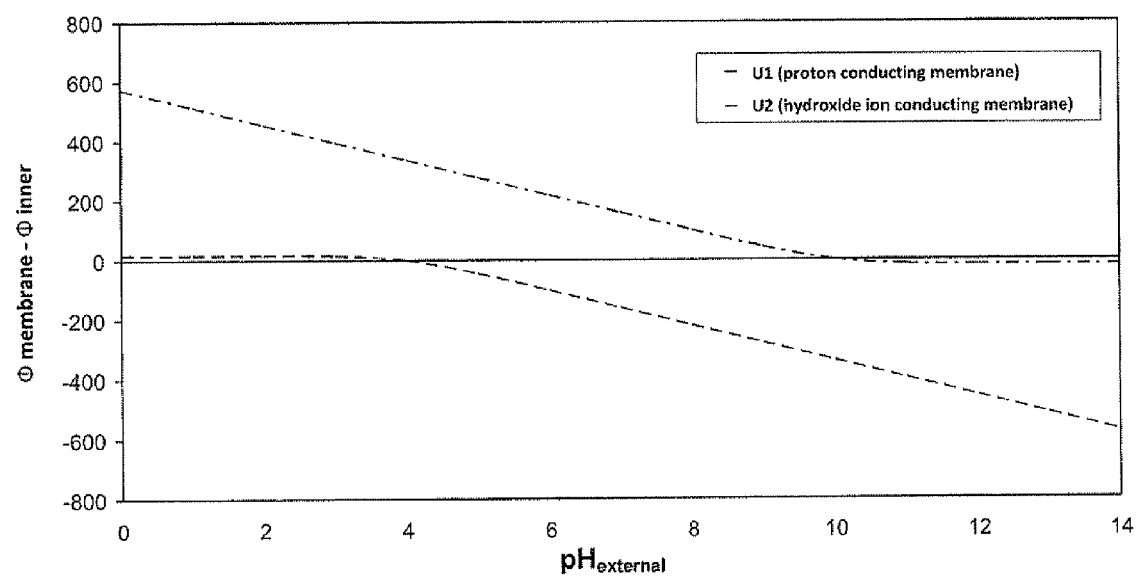
FIG. 5 a graph showing the measuring signals of the first measuring transducer and second measuring transducer of the measuring arrangement illustrated in FIG. 4.

An expanded measuring range compared to measurement with only one measuring transducer is also available from the arrangement shown in FIG. 4: FIG. 5 shows, by way of example, curves of the measuring signals (potential differences between the potential sensing elements) of the potentiometric measuring transducers 400 and 500 as a function of the pH value of measured medium M, wherein potential sensing elements 440 and 540 register, respectively, potentials in the region of the relative position 0.5 within membranes 10 and 20, respectively. As can be seen from the graph, in the pH value range between 0 and 4, the measurement signal of measuring transducer 400 can be used for determining the pH value. In the pH value range between 4 and 10, the two measuring signals can be used for determining the pH value, wherein, in this region, the functionality of the measuring arrangement can be checked by comparing the pH values determined using both measuring signals. In the pH value range between 10 and 14, the pH value can be ascertained from the measurement signal of measuring transducer 500.

Figure 6:
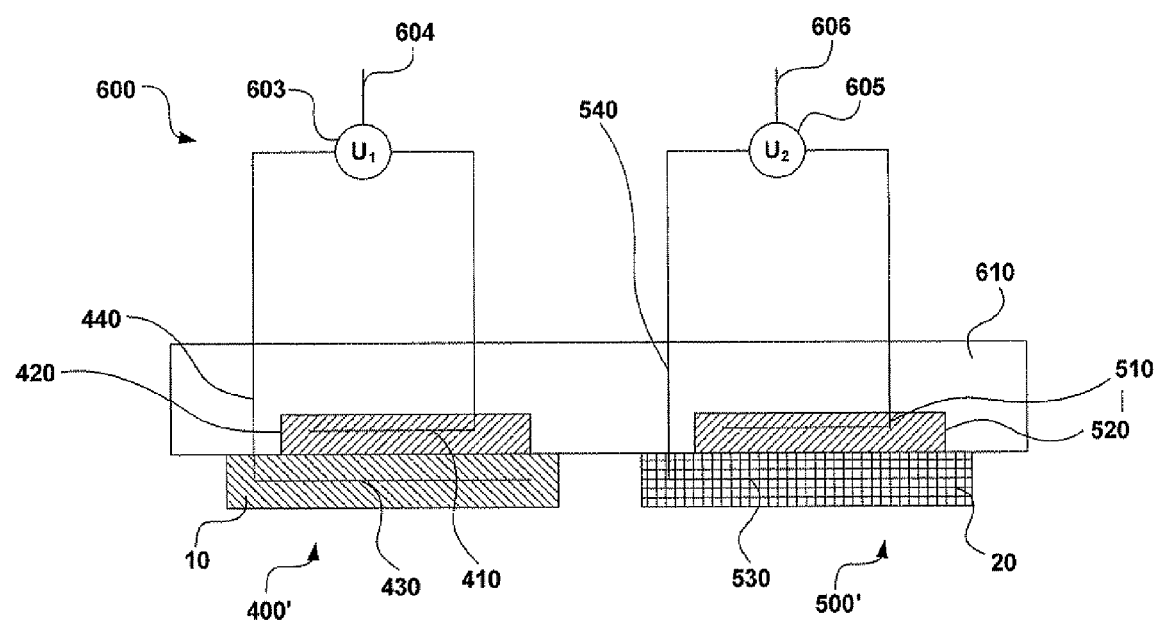
FIG. 6 a measuring arrangement with a first potentiometric measuring transducer intergrated in a chip and a second potentiometric measuring transducer intergrated in the chip, wherein the first transducer has a proton conducting membrane and the second transducer has a hydroxide conducting membrane.

FIG. 6 shows a schematic longitudinal section through a miniaturized embodiment of the measuring arrangement shown in FIG. 4. This embodiment can be manufactured, for example, in the form of a chip. The measuring arrangement 600 comprises two potentiometric measuring transducers 400', 500', which are intergrated in a shared platform 610, e.g. an injection molded plastic chip. Platform 610 includes a first cavity, which is filled with inner electrolyte 420, for example, a pH buffered 3M KCl solution with a pH value greater than or equal to 10. The cavity is sealed to liquid by means of membrane 10 affixed to platform 610 so that the inner electrolyte contacts the surface of membrane 10 facing the cavity and is constrained by membrane 10 from leaking from the cavity. Membrane 10 is selectively proton conducting. Extending into inner electrolyte is the first potential sensing element 410, for example, a chloridized silver wire, which, for example, by way of at least one via extending through platform 610 and one or more conductive traces extending on a surface of platform 610, is connected to measurement circuit 603, which is preferably also arranged on platform 610. Measurement circuit 603 can alternatively also be arranged separately from platform 610. Second potential sensing element 440' has a lattice 430, for example, comprising platinum, embedded in membrane 10. Lattice 430 is electrically conductively connected to measurement circuit 603 by means of a contact led through platform 610 outside the cavity containing inner electrolyte 420.

Platform 610 additionally has a second cavity, which is filled with inner electrolyte 520, for example, a pH buffered 3M KCl solution with a pH value of less than or equal to pH 4. The cavity is sealed to liquid by means of membrane 20 affixed to platform 610, so that the inner electrolyte 520 contacts membrane 20 on its side facing the cavity, but is constrained by membrane 20 from leaking from the cavity. Membrane 20 comprises a hydroxide conducting polymer. A first potential sensing element 510, for example, a chloridized silver wire, extends into inner electrolyte 520. A second potential sensing element 540 has a lattice 530 as described in FIG. 4, for example, likewise comprising platinum, embedded in membrane 20. Lattice 530 is electrically conductively connected to a measurement circuit 605 through platform 610 by a contact led outside the cavity containing inner electrolyte 520. First potential sensing element 510 is also connected to measurement circuit 605. The connection of the potential sensing elements 510 and 540 to measurement circuit 605 can be embodied by means of vias led through platform 610 and/or by means of conductive traces arranged on a surface of platform 610. Measurement circuit 605 is preferably arranged on platform 610. However, it can also be arranged at least partially separated from platform 610. Platform 610 can especially be embodied as a chip or microchip.

The two measuring circuits 603 and 605 are embodied to register potential differences between their two potential sensing elements 410, 440, and 510, 540, respectively, connected to them and to output these potential differences, or a signal derived therefrom by further processing, measurement signals via their signal outputs 604 and 605 to, for example, a superordinated unit.

The invention claimed is:

1. A measuring transducer embodied to produce and output a measurement signal dependent on an activity of a target ion present in a measured medium, comprising:
    at least one membrane conducting the target ion in a region provided for contact with the measured medium;
    a first potential sensing element; and
    a second potential sensing element, wherein:
    at least one section of said second potential sensing element is arranged in the interior of said at least one membrane; and
    said first potential sensing element is arranged in an inner electrolyte, which is separated from the measured medium by said at least one membrane and is in contact with said at least one membrane.

2. The measuring transducer as claimed in claim 1, further comprising:
    at least one additional measuring sensor for registering a property of said inner electrolyte and/or said at least one membrane.

3. The measuring transducer as claimed in claim 1, wherein:
    said at least one membrane is a polymer membrane selectively conducting the target ion.

4. The measuring transducer as claimed in claim 1, wherein:
    the measuring transducer is embodied as a potentiometric probe.

5. The measuring transducer as claimed in claim 1, wherein:
    the measuring transducer is embodied to output as a measurement signal a potential difference between said first potential sensing element and said second potential sensing element or a digital signal derived from the potential difference.

6. The measuring transducer as claimed in claim 1, wherein:
    said inner electrolyte is pH buffered.

7. The measuring transducer as claimed in claim 1, wherein:
    said inner electrolyte contains the target ion in a known concentration.

8. The measuring transducer as claimed in claim 1, wherein:
    said inner electrolyte contains dissolved halogen ions; and
    said first potential sensing element comprises a difficultly soluble salt of the halogen ions dissolved in said inner electrolyte.

9. The measuring transducer as claimed in claim 1, wherein:
    said second potential sensing element has a first section formed as one of: a lattice, loop, spiral or meander embedded in said at least one membrane and a second section electrically conductively connected to said first section and electrically insulated from said at least one membrane and from said inner electrolyte.

10. The measuring arrangement, comprising one or more measuring transducer(s) as claimed in claim 1.

11. The measuring arrangement as claimed in claim 10, comprising:
    a first potentiometric measuring transducer with a selectively $H^+$ ion conducting, polymer membrane, arranged in a region provided for contact with the measured medium; and
    a second potentiometric measuring transducer having at least one $OH^-$ ion said conducting, second polymer membrane conducting second polymer membrane, arranged in a region provided for contact with the measured medium.

12. The measuring arrangement as claimed in claim 11, wherein:
    said first measuring transducer has a first potential sensing element and a second potential sensing element;
    at least one section of said second potential sensing element is arranged in the interior of said first polymer membrane, in order to produce and to output an electrical potential dependent on activity of $H^+$ ions present in the measured medium, and said first potential sensing element is arranged in a pH buffered, inner electrolyte, which is separated from the measured medium by said first membrane and is in contact with said first membrane, in order to produce and to output an electrical potential largely constant over time; and the measuring arrangement is embodied to determine a first pH value and/or a first pOH value from a potential difference measured between said first potential sensing element and said second potential sensing element of said first measuring transducer or a signal derived from the potential difference;

said second potentiometric measuring transducer has a first potential sensing element and a second potential sensing element;

said second potential sensing element is arranged in the interior of said second membrane, in order to produce and to output an electrical potential dependent on activity of $H^+$ ions present in the measured medium;

said first potential sensing element is arranged in a pH buffered inner electrolyte, which is separated from the measured medium by said second membrane and is in contact with said second membrane, in order to produce and to output an electrical potential largely constant over time; and the measuring arrangement is embodied to determine a second pH value and/or a second pOH value from a potential difference measured between said first potential sensing element and said second potential sensing element of said second measuring transducer or signal derived from the potential difference.

13. The measuring arrangement as claimed in claim 12, wherein:

said inner electrolyte of said first measuring transducer has a pH value, which differs from the pH value of said inner electrolyte of said second measuring transducer, is less than the pH value of said inner electrolyte of said second measuring transducer.

14. The measuring arrangement as claimed in claim 10, wherein:

one or more measuring transducers are integrated in a single component, on a chip.

\* \* \* \* \*